United States Patent [19]
Cathey et al.

[11] Patent Number: 5,660,993
[45] Date of Patent: *Aug. 26, 1997

[54] DISPOSABLE DEVICE IN DIAGNOSTIC ASSAYS

[75] Inventors: Cheryl A. Cathey, Palo Alto; Tom Saul, Moss Beach; Nicole D. Bloom, San Francisco; Hans O. Ribi, Hillsborough; Henry L. Schwartz, San Francisco; Jeffrey B. Langford, Pacifica, all of Calif.

[73] Assignee: Biocircuits Corporation, Sunnyvale, Calif.

[*] Notice: The term of this patent shall not extend beyond the expiration date of Pat. No. 5,399,486.

[21] Appl. No.: 296,489

[22] Filed: Aug. 24, 1994

Related U.S. Application Data

[63] Continuation-in-part of Ser. No. 179,749, Jan. 7, 1994, Pat. No. 5,503,985, which is a continuation-in-part of Ser. No. 19,469, Feb. 18, 1993, Pat. No. 5,399,486.

[51] Int. Cl.[6] ..................... G01N 33/543; G01N 33/558
[52] U.S. Cl. .................. 435/7.9; 422/55; 422/57; 422/58; 422/61; 435/287.1; 435/287.2; 435/288.1; 435/288.2; 435/288.3; 435/288.4; 435/288.5; 435/810; 435/973; 436/164; 436/165; 436/514; 436/518; 436/524; 436/527; 436/528; 436/805; 436/807; 436/808; 436/810
[58] Field of Search ..................... 422/55, 57, 58, 422/61; 435/7, 9, 810, 973, 287.1, 287.2, 288.1, 288.2, 288.3, 288.4, 288.5; 436/164, 165, 514, 518, 524, 527, 528, 805, 807, 808, 810

[56] References Cited

U.S. PATENT DOCUMENTS

| | | | |
|---|---|---|---|
| 3,799,742 | 3/1974 | Coleman | 422/58 |
| 4,012,198 | 3/1977 | Finter et al. | 424/12 |
| 4,426,451 | 1/1984 | Columbus | 436/518 |
| 4,855,240 | 8/1989 | Rosenstein et al. | 436/514 |
| 4,859,421 | 8/1989 | Apicella | 422/61 |
| 4,918,025 | 4/1990 | Grenner | 436/165 |
| 4,963,498 | 10/1990 | Hillman et al. | 436/69 |
| 5,198,368 | 3/1993 | Khalil et al. | 436/518 |
| 5,207,988 | 5/1993 | Lucas | 422/73 |
| 5,217,905 | 6/1993 | Marchand et al. | 436/518 |
| 5,223,219 | 6/1993 | Subramanian et al. | 422/55 |
| 5,399,486 | 3/1995 | Cathey et al. | 435/7.9 |

FOREIGN PATENT DOCUMENTS 0430248   6/1991   European Pat. Off. .

Primary Examiner—James C. Housel
Assistant Examiner—Christopher L. Chin
Attorney, Agent, or Firm—Bertram I. Rowland; Bret E. Field; Flehr, Hohbach, Test, Albritton & Herbert

[57] ABSTRACT

A disposable diagnostic assay device and method for its use are provided. The device comprises a sample addition port in fluid communication with at least one main channel. The main channel comprises, in the direction of fluid flow, a main reagent area in fluid communication with an incubation area and a waste area. In fluid communication with the main channel is at least one side reagent channel. The side reagent channels comprise, in the direction of fluid flow, a liquid addition port and a side reagent area in fluid communication with the main channel at a region of the main channel upstream from the incubation area. Agitation means may be included in the at least one of the main and side reagent areas and/or the incubation area. Capillary valves may be located at various positions along the main and side reagent channels upstream from the incubation area, providing for control over fluid flow through the device. Applications in which the device finds use include diagnostic assays employing signal producing systems based on the interactions of specific binding pair members, where optical signals are related to the presence of analyte.

12 Claims, 8 Drawing Sheets

DISPOSABLE DEVICE IN DIAGNOSTIC ASSAYS

CROSS REFERENCE TO RELATED APPLICATIONS

This application is a continuation-in-part of application Ser. No. 08/179,749, filed Jan. 7, 1994 now U.S. Pat. No. 5,503,985; which is a continuation-in-part of application Ser. No. 08/019,469 filed Feb. 18, 1993 now U.S. Pat. No. 5,399,486.

INTRODUCTION

1. Technical Field

The technical field of this invention is disposable devices for use in analyte detection assays.

2. Background

Despite the numerous strides that have been made in the last two decades in the development of diagnostic reagents and instruments, efforts continue to make diagnoses more accurate, simpler, and more available to non-technical personnel in a wide variety of environments. There is continuing interest in being able to carry out individual assays by non-technical personnel at such sites as doctor's offices, clinics, the home, rest homes, and the like. In order to ensure that non-technical individuals may accurately perform these assays, it is essential that the protocols be simple and that there be few, if any, measurements. Further, the readings must be relatively automatic.

In designing these types of assays, it is desirable to have a disposable device which can be used individually for a particular assay determination and then discarded. The disposable device can provide the various members of the signal producing system which are necessary for the assay determination, serve to ensure the appropriate mixing of the reagents of the signal producing system, and allow for the proper fitting of the device into an automated instrument which provides the final determination. Thus, in using the device, the operator need only add sample and then read the result. In this manner, one can be relatively assured that assay determinations may be made rapidly and with a minimum opportunity for error in quantitation.

Clinical laboratories also provide many opportunities for measuring an analyte in an individual assay determination. Frequently, particular analytes may be determined only a few times in any one day, so that individual assays will be the most efficient method of performing a particular analyte determination. Where one can use a disposable device which only requires the addition of the sample to the disposable device, significant savings in labor may be realized, because individuals of high technical qualification would not be required for operation of the assay and the accuracy of the analyte determination would be relatively assured.

In response to this need for disposable assay devices, the industry has responded with devices which allow for the performance of the assay protocol, with minimal measurement and input from the operator, while allowing for sensitive and accurate detection of the amount of analyte in a sample. Despite the development of such disposable devices, there are problems with currently available designs. Long-standing difficulties have included problems with efficiently mixing participating reagents with sample, problems in efficient washing to remove unbound reagents from a measurement area, problems in controlling the fluid flow through the assay device, problems in controlling the timing of interaction between members of the signal producing system in the device, and the like. Further, problems have been encountered in designing a disposable device which has a basic design that is sufficiently flexible so that it can be used in a variety of different assays, thereby limiting the possibility of using the same structural configuration for a wide variety of assays.

Thus, there is a need for the development of improved disposable assay devices. The improved devices should provide for increased ease and simplicity of use, while consistently providing a reliable result. The improved devices should also provide for improved control and reproducibility over reagent interaction and fluid flow through the device. Furthermore, the device should have a structural configuration that is adaptable for use in a wide variety of diverse assays.

Relevant Literature

Enzyme immunoassays are described in: Tijssen, Practice and Theory of Enzyme Immunoassays(Elsevier) 1985; Wisdom, "Recent progress in the Development of Enzyme Immunoassays," Ligand Rev. (1981) 3: 44–49; and Ishikawa, "Development and Clinical Applications of Sensitive Enzyme Immunoassays for Macromolecular Antigens-A Review," Clin. Biochem. (1987) 20:375-385. Fluorescence Immunoassays are described in: Smith et al., "A Review of Fluoroimmunoassay and Immunofluorometric Assay," Ann. Clin. Biochem. (1981) 18:253–274; Hammila, "Fluoroimmunoassays and Immunofluorometric Assays," Clin. Chem. (1985)31: 359-370; Diamandis, "Immunoassays with Time-Resolved Fluorescence Spectroscopy: Principles and Applications," Clin. Biochem. (1988)21: 139–150. Chemiluminescent Immunoassays are described in: Kricka & Thorpe, "Luminescent Immunoassays," Ligand Rev. (1981) 3: 17–24; Seitz, "Immunoassay Labels Based on Chemiluminescence and Bioluminescence," Clin. Biochem. (1984) 17:120–125; Weeks & Woodhead, "Chemiluminescence Immunoassay," J. Clin. Immunoassay (1984) 7: 82–89. Fluorescence polarization techniques are described in: DeGrella, "Fluorescence Polarization: A Review of Laboratory Applications," Amer. Biotech. Lab. (1988) 6: 29–34; Jolley et al., "Fluorescence Polarization Immunoassay. III. An Automated System for Therapeutic Drug Determination," Clin. Chem. (1981) 27: 1575–1579; Dandliker et al., "Fluorescence Methods for Measuring Reaction Equilibria and Kinetics," Meth. Enzymol. (1978) 48: 380–415. Immunoassays are generally described in: Collins, Alternative Immunoassays (John Wiley 1985); Freytag, "The Future of Immunodiagnostics," J. Clin. Immunoassay (1991) 14:239–244 and Gosling, "A Decade of Development in Immunoassay Methodology," Clin. Chem. (1990) 36: 1408–1427.

SUMMARY OF THE INVENTION

A disposable assay device and methods for its use are provided. The device comprises a sample addition port in fluid communication with at least one main channel. The main channel comprises, in the direction of fluid flow, a main reagent area in fluid communication with an incubation area and a waste area. In fluid communication with the main channel is at least one side reagent channel. The side reagent channels comprise, in the direction of fluid flow, a liquid addition port and a side reagent area in fluid communication with the main channel at a region upstream from the incubation area. The main and side channels are conveniently located in a housing comprising a top and bottom plate, where an optically clear window is present over the incubation area for assay signal detection. Efficient mixing of reagent in any of the reagent areas and/or in the incubation area may be accomplished by inclusion of agitation means in these areas. Control of fluid flow through the device is enhanced through placement of at least one capillary valve at locations in the main and side channels upstream from the incubation area.

The device finds use in analyte detection assays where the signal producing system used in the assay is based on interactions between specific binding pair members and an optical signal is related to the presence of analyte in the sample.

DESCRIPTION OF THE SPECIFIC EMBODIMENTS

Figure 1:
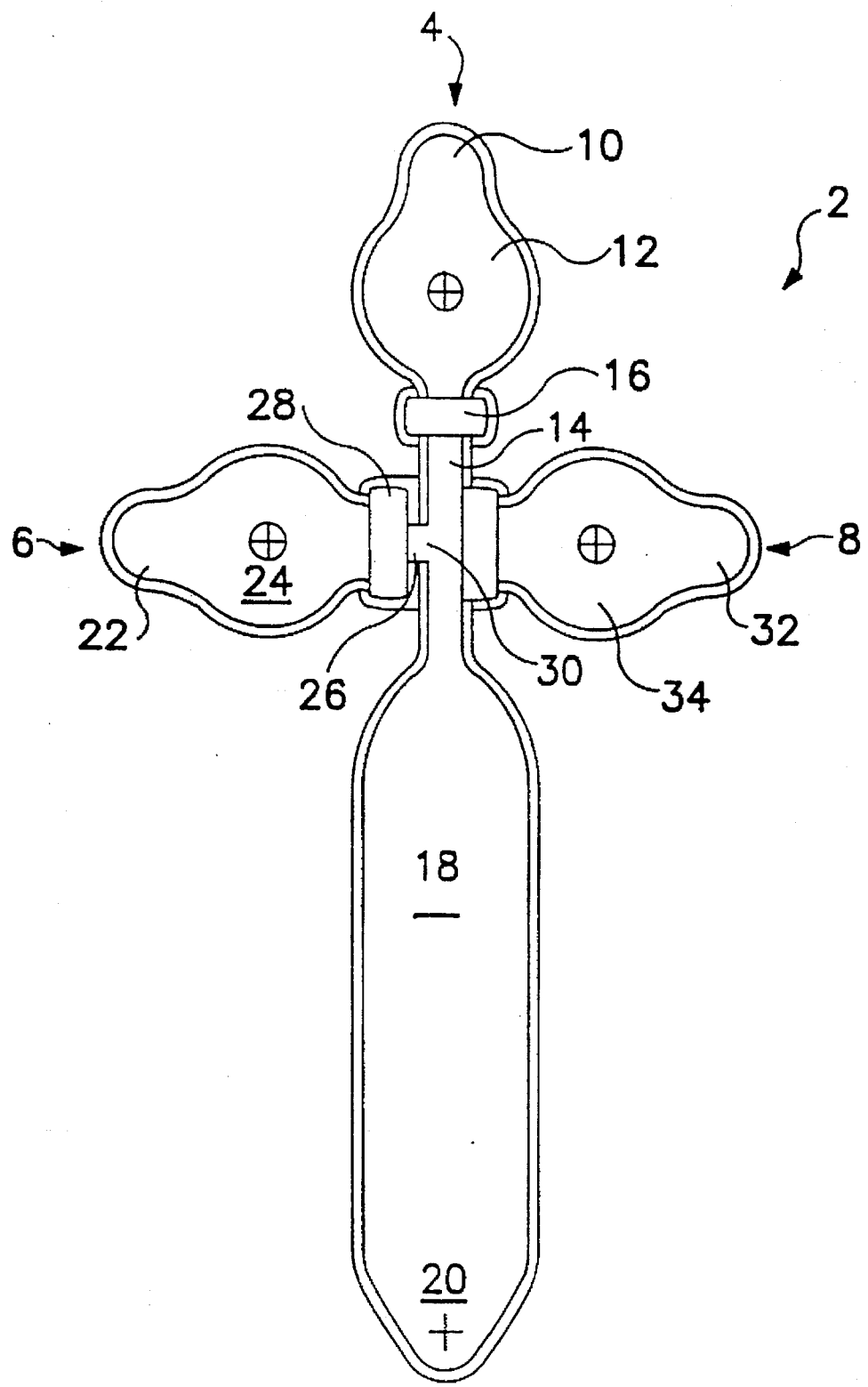
FIG. 1 is an overhead view of an assay path according to the subject invention.

A disposable assay device and methods for its use are provided for determining the presence of an analyte in a sample. The device comprises a sample addition port in fluid communication with at least one main channel. The main channel comprises, in the direction of fluid flow, a main reagent area in fluid communication with an incubation area and a waste reservoir. In fluid communication with the main channel is at least one side reagent channel. The side reagent channels comprise, in the direction of fluid flow, a liquid addition port and a side reagent area, where the side reagent channel is in fluid communication with the main channel at a region upstream from the incubation area. To provide for homogeneous dispersal of signal producing system members in the sample, agitation means may be provided in at least one of the main and side reagent areas and/or the incubation area. Capillary valves located at various positions along the main and side reagent channels upstream from the incubation area may be used to control fluid flow through the device.

The device comprises a sample addition port through which sample is introduced. In fluid communication with the sample addition port is at least one main channel. The main channel of the subject device originates beneath the sample addition port in a sample receiving region. The sample receiving region serves to receive the sample and provide a conduit between the sample receiving region and the first reagent area. Preferably, the sample receiving region is sufficiently long to ensure that air outside the device cannot directly access the main reagent area, since air in the reagent area may adversely interfere with the assay being conducted in the device.

In fluid communication with the sample receiving region is the main reagent area. The main reagent area may serve a variety of purposes. First, a member or members of the signal producing system, e.g. dry reagent, may be stored in the main reagent area, so that upon entry of sample into the main reagent area, dry reagent is rehydrated and available for reaction in the assay. Further, the main reagent area may serve as a convenient location where the sample temperature may be modulated, e.g. raised or lowered, as desired for the particular assay being carried out. Finally, the main reagent area may comprise agitation means, so that the main reagent area serves as a mixing chamber where member of the signal producing system is homogeneously dispersed throughout the sample.

The main reagent area is in fluid communication with at least one incubation area. In some embodiments, the border between the reagent and incubation areas may be so indefinite that the two regions may be considered one region. However, the two regions will typically be separated by a main transport channel. The main transport channel may serve as a conduit of sample from the main reagent area to the incubation area. The main transport channel may further serve a variety of additional functions. Depending on the nature of the assay, the main transport channel may serve as a storage area for various reagents which may be diffusibly or non-diffusibly bound to the walls of the transport channel. For example, antibodies may be present which serve to remove one or more components from the sample, e.g. cells, interfering components, etc. Chemical reagents may also be located in the main transport channel to change the pH, redox potential or other characteristics of the sample. In this way, sample introduced in the sample port may be modified as necessary for the portion of the assay which is conducted in the incubation area. Finally, the main transport channel may serve as the receiving area, where fluid from the side reagent channels enters, and combines with, the main channel.

In fluid communication with, and downstream from, the main transport channel is the incubation area. The incubation area is where the signal which is related to the presence of analyte is produced. On one wall of the incubation area, usually the top wall, will be an optically clear window which provides for viewing of the signal generated by the particular assay being performed in the incubation area. Opposite the top wall is a bottom wall. Diffusibly or non-diffusibly bound to the top and/or bottom wall, usually the top wall, will be members of the signal producing system. In one embodiment, an assay platform may be included which comprises members of the signal producing system. A plurality of incubation areas may be included in the main channel, where fluid flows from one incubation area to another sequentially. Where the main channel comprises a plurality of incubation areas, one may perform different assays in each of the incubation areas on the same sample.

Located to one side of the incubation area, usually at the far side opposite the side adjacent the main transport channel, will be the waste area. The waste area serves to receive the unreacted sample and/or various wash fluids which flow through the incubation area during a particular assay.

In addition to the main channel, the subject device also comprises at least one side reagent channel or flow path, and more usually comprises two side reagent channels. Side reagent channels provide for the sequential addition of one or more members of the signal producing system into the incubation area. Furthermore, the side reagent channels provide alternative means of introducing liquid, e.g. wash fluid, into the incubation area, so that one may avoid contamination with reagent remaining in the main reagent area.

Analogous to the main channel, the side reagent channels of the subject device originate with a liquid addition port. In fluid communication with, though not directly below, the liquid addition port will be the side reagent area. Preferably, the side reagent area is a sufficient distance from the liquid addition port so as to preclude direct access to air outside the device to the side reagent area, where air in the side reagent are may interfere with the assay being conducted in the device. As with the main reagent area described above, the side reagent area may serve as an area where members of the signal producing system are stored, as an area where the temperature of the liquid may be modulated and as an area for homogeneously dispersing reagent throughout the liquid. Connecting the side reagent area with the main channel in fluid communication at a region of the main channel upstream from the waste area, e.g. at the incubation area or main transport channel, is a side reagent transport channel. The side reagent transport channel serves as a conduit for liquid, and any member of the signal producing system present therein, from the side reagent area to the main channel.

To assist in homogeneous dispersal of the various signal producing system members in the sample and other liquid mediums flowing through the device, an agitation means may be provided in at least one of the main and side reagent areas and/or the incubation area. The agitation means serves to provide sufficient fluid flow so that dry reagent present in the vicinity of the agitation means is efficiently hydrated and homogeneously distributed throughout the fluid. Agitation means includes airflow, shaking, ultrasonic techniques, suction techniques, e.g. where reagent is dehydrated onto a porous membrane and fluid in sucked through the membrane resulting in hydrated reagent, and mechanical means, preferably mechanical mixing means. Suitable mechanical mixing means include mixing means fabricated from magnetic and paramagnetic materials, and may take diverse forms, including propellers, pins, dumbbells, balls, wires, perforated sheets; discs with fins and the like. In a preferred embodiment, the agitation means is an impeller device. Where the material from which the mixing means is magnetic or paramagnetic, agitation is conveniently accomplished by applying a moving magnetic field above or below the device, or alternatively, by moving the device through a stationary magnetic field. The rate and/or timing of mixing may be controlled as needed to cause the desired level of agitation.

Control of fluid flow through the main and side reagent channels may be enhanced though use of a variety of means. For example, where one desires to enhance fluid flow through a device, one may provide for hydrophilic regions in the channel at the appropriate region, where the hydrophilic region serves to attract and draw fluid through that region. Alternatively, where one wishes to slow or impede fluid flow through a particular region of the channel, one may provide for hydrophobic areas in that particular region. Another means of enhancing control of fluid flow through the device is to employ one or a plurality of capillary valves, which may be located at various positions along the main and/or side reagent flow paths, usually being positioned at a region of the channel upstream from the incubation area.

The device may be varied as to size, usually being at least about 1 cm×1 cm and not more than about 20 cm×20 cm, preferably having a shorter dimension in the range of about 4–7 cm and in a longer direction by about 5–10 cm. While for the most part, the device may be any convenient shape, generally, it will be rectangular where the edges may be modified by rounding, cutting the corner(s), or other modification which will allow for easy handling and adapting the device to an instrument with which it is used. The thickness of the device will generally vary from about 1 mm 3 cm, more usually from about 1.5–3 mm.

The device may comprise one or more assay paths, where an assay path comprises the main and side reagent channels. Inclusion of two assay paths allows for the running of a control with the sample or running two assays on portions from the same sample.

Also included in the device may be a reference region which serves to provide an indication of the operability of the members of the signal producing system being employed. For example, where a signal producing system comprises enzyme and substrate, where the substrate is converted to a detectable product, the reference zone may comprise dehydrated enzyme and substrate. When the device is used, a drop of fluid is placed in the reference zone. Appearance of enzyme product indicates the enzyme is active, thus indicating that the enzyme in the device will be operative. The reference region will be positioned in the device at a region which is not in fluid communication with the assay path(s) of the device, so as not to interfere with an assay being conducted with the device.

Applications in which the subject device may find use include assays where the signal producing system is based on interactions between specific binding pair members and an optical signal is generated by the system which is related to the presence of analyte in the assayed sample.

In carrying out such an assay in the device, one may assay any type of liquid, where the liquid may be assayed directly or may be subjected to prior treatment, depending upon the nature of the liquid and the analyte of interest. The liquid may contain a sample or be a sample from any source, such as a physiological source, e.g. blood, serum, plasma, urine, saliva, spinal fluid, lysate, nasal pharyngeal aspirates etc.; sample of ecological interest, e.g. water, soil, waste streams, organisms, etc.; food, e.g. meat, dairy products, plant products, other organic matter etc.; drugs or drug contaminants in processing; or the like.

The analyte may be any compound which can be detected and is a member of a specific binding pair, either ligand or receptor. The term "receptor" is used arbitrarily, since its origin had to do with surface membrane proteins, where the compound which bound to the surface membrane protein was referred to as a ligand. Receptors include naturally occurring receptors, e.g. enzymes, lectins, surface membrane proteins, antibodies, recombinant proteins, etc., synthetic receptors, nucleic acids, c-glycosides, carbohydrates, gangliosides, chelating compounds, etc. For the purpose of the subject invention, it is sufficient that two molecules have a significant affinity for each other, where the binding constant will usually be at least about $10^5$ mol$^{-1}$ and one may choose to refer to either member as the receptor. Compounds of interest have to some degree been indicated by indicating the various sample sources. The analyte may be any type of compound, e.g. small organic molecules, peptides and proteins, sugars, nucleic acids, complex carbohydrates, viruses, bacteria particles, lipids and combinations thereof, naturally occurring or synthetic or combinations thereof, so long as there is a complementary binding member. The analytes will frequently include drugs, both naturally-occurring and synthetic, various components of animals, including humans, such as blood components, tissue components, and the like; microorganisms, such as bacteria, fungi, protista, viruses, and the like; components of waste streams or products or contaminants of Such products in commercial processing; components in the environment, particularly contaminants, such as pesticides, microorganisms, and the like.

Depending upon the nature of the sample, the sample may be subjected to prior treatment, such as extraction, distillation, chromatography, gel electrophoresis, dialysis, dissolution, centrifugation, filtration, cell separation, and the like. For blood, one may wish to remove red blood cells to provide plasma or serum but their removal is not necessary. Various media may be employed, which will allow for providing for a sample solution or dispersion which can be used in the subject device.

After appropriate pretreatment, if any, the sample in liquid form is then introduced into the sample port. The volume of sample may range from about 1 µl to about 0.5 ml, more usually from about 10 µl to 250 µl, preferably from about 25 µl to 170 µl. The sample is drawn from the sample receiving region beneath the sample application port by capillary action into the main reagent area. In the main reagent area, the sample may combine with a member of a signal producing system. If the main reagent area comprises agitation means, the sample may be agitated, thereby hydrating any dry signal producing system member present in the main reagent area and dispersing the hydrated member homogeneously throughout the sample. Depending on the particular signal producing system, a variety of members may be included in the main reagent area, including antibodies or fragments thereof, antibody/enzyme conjugates, antibodies labeled with a dye molecule, specific for analyte or binding member in the incubation area, and the like.

The sample flows from the main reagent area into the main transport channel. Where the main reagent area and the main transport channel are separated by a capillary valve, the capillary valve may be filled to provide for fluid flow into the main transport channel. Further, the vigor of agitation in the main reagent area may be increased to provide the necessary force to move sample into the transport channel. As the sample proceeds down the main transport channel, it dissolves and/or reacts with any reagent which may be present in the transport channel.

As the sample flows into the incubation area, it combines with other members of the signal producing system which are present in the incubation area. Other members of the signal producing system which may be present in the incubation area may be members of specific binding pairs, fluorescent production layers as described in U.S. application Ser. No. 08/089,975, the disclosure of which is incorporated herein by reference and lipid layers as described in U.S. Pat. No. 5,156,810 and U.S. application Ser. No. 08/084,884, the disclosures of which are incorporated herein by reference.

Signal production systems which find use in the application may involve competition or cooperation. In the case of competition, the conjugate will bind to either the analyte or binding sites in the incubation area, e.g. on the walls of the incubation area, on an assay platform in the incubation area, on a membrane in the incubation area, and the like. By having a limited number of conjugate molecules, the number of conjugate molecules which can bind to the complementary binding member will be inversely proportional to the number of molecules of analyte in the sample. Thus, the number of labels which ultimately become bound in the incubation area will be inversely proportional to the number of analyte molecules in the sample. This approach will normally be employed with small analytes, particularly haptenic analytes, where the analyte can only bind to a single receptor.

By contrast, with larger analytes, which are polyepitopic, one has the opportunity for two receptors to bind simultaneously. In this way, the analyte may serve as a bridge between the complementary binding member bound to the membrane and the complementary binding member which is labeled. One may also use the competitive protocol, by having the specific binding pair member of the conjugate capable of competing with the analyte for binding to the bound binding member.

Where a member of the signal producing system is a membrane, the membrane in the incubation area may be divided up into a plurality of sections, where each section may have the same or different specific binding pair member. In this way, the sample may be assayed simultaneously for a number of different analytes. Depending upon the nature of the different analytes, the same or different members of the signal producing system, e.g. conjugates, would be present in the incubation area. The assay could be carried out in the same way, except at the time of reading, one would specifically address different regions of the membrane to identify the signal coming from each of the individual regions.

After sufficient time for substantially complete reaction of the analyte in the incubation area, the incubation area may be washed to remove substantially all of the sample and unreacted members of the signal producing system. A buffered aqueous solution may be used which is appropriate for maintaining the binding of the specific binding pair members. Buffer may be introduced through the main sample addition port or one of the side reagent ports, where the buffer travels down the main or side reagent channels respectively and into the incubation area. Usually, the volume of the wash solution will be at least about equal to the volume of the sample and may be 40-fold more or greater than the volume of sample, and preferably at least about 2-fold greater than the volume of sample. Washing of the incubation area may be enhanced with agitation, where agitation means are included in the incubation area.

Depending upon the signal producing system employed, it may be necessary to introduce an additional member or members of the signal producing system into the incubation area after the sample has been introduced. To introduce the additional member or members (which may be stored in the side reagent area) liquid, e.g. buffer, is introduced into the liquid addition port, whereby it flows into the side reagent area. In the side reagent area, the additional member will combine with the liquid and be carried into the incubation area, where it may participate in the signal producing system. For example, where an enzyme is the label used in the signal producing system, the enzyme or enzyme conjugate may be contained within the side reagent area. It will be necessary to provide substrate to obtain a detectable product, where the detectable product is either directly detectable or acts to modulate the signal of another member of the signal producing system, e.g. binding pair members, a fluorescent production layer, a fluorescent lipid membrane. One of the side reagent areas could house this substrate. Upon addition of buffer to the liquid addition port, the substrate is hydrated and then flows into the main flow path, where it is converted by the enzyme in the incubation area to a detectable product. Alternatively, where the label is a chemiluminescent label, members which may be introduced into the incubation area via the side reagent channels will include reagents necessary for reacting with the label to provide the luminescent signal. In another signal producing system which may find use in the subject device, additional members may be reagents which directly or indirectly modulate the fluorescence of a fluorescent lipid membrane in the incubation area. Direct modulation may result from binding events, where the binding events change the conformation of the lipid layer thereby changing it optical properties. Indirect modulation may result from binding events which change the environment of the lipid layer, e.g. the pH, temperature, mechanical stress, ionic strength and the like. Optical properties which may be directly or indirectly modulated in response to the presence of analyte include changes in the emission or absorption characteristics of the lipid layer. Alternatively, where diffraction particles are the detectable label, as described in co-pending application Ser. No. 07/939,585, filed Sep. 3, 1992, the diffraction particles may be stored in the dry reagent area and upon hydration, flow into the incubation area and participate in the assay, where participation may comprise binding to specific binding pair member on the platform or agglutinating in the incubation area in a manner which is dependent upon the amount of analyte present in the area. Introduction of the additional member or members into the incubation area may be followed by additional washings to again remove unreacted members of the signal producing system, as needed.

The final step in using the subject device in an assay is to read the detectable signal. The detectable signal is read through the optically clear window located opposite the assay platform. Reading the detectable signal may comprise a single measurement or series of measurements, e.g. to determine a rate br to wait for background signal to fade, depending on the assay. Further, one may read the signal generated and compare it to the signal read from a control, where the control comprises a predetermined amount of analyte, including no analyte. Depending upon the signal producing system, it may be necessary to irradiate the incubation area so as to obtain a detectable signal, e.g. where a fluorescent label is employed.

The structural configuration of the subject device provides the opportunity to run a wide variety of assays using diverse signal producing systems. Although partially indicated previously, labels which may be employed are those that provide an optical signal and include fluorescent and chemiluminescent labels, enzymes which convert substrate to detectable product, particles for aggregation and diffraction assays, dye molecules attached to antibodies, and the like. Optical signals which may be detected through the optically clear window and related to the presence and/or amount of analyte in the sample include emissions, e.g. from fluorescent and chemiluminescent labels, fluorescence quenching of a member of the signal producing system, light scattering and diffraction, such as that associated with aggregation systems or diffraction particles, e.g. agglutination of red blood cells, changes in refractive index, e.g. plasmon resonance, changes in absorption or transmittance, e.g. color changes of polydiacetylene layers from blue to red, modulation of linear and circular birefringence and/or dichroism of a polydiacetylene film, fluorescent enhancement of polydiacetylene films, and the like.

Additional applications in which the subject device may find use include nucleic acid amplification protocols, such as those based on polymerase chain reaction (PCR) as described in Sambrook, Fritsch & Maniatis, Molecular Cloning-A Laboratory Manual (Cold Spring Harbor Laboratory Press, 1989) and ligase chain reaction (LCR) as described in Laffler et al., "The Ligase Chain Reaction in DNA-Based Diagnosis," Ann. Biol. Clin. (1993) 51: 821–826. The subject device may also be used in conjunction with biosensors which provide for mass detection methods, such as those described in Tailor, R. F., Biosensor Technology Applications and Market Analysis (Burlington Mass.; Decision Resources) and Turner, Karube and Wilson, Biosensors: Fundamentals & Applications (Oxford University Press) 1987.

The various applications of the fluid to the disposable device can be conveniently carried out automatically with an appropriate instrument. Thus, the instrument may measure the sample and wash volumes introduced into the device, time the incubations, maintain constant temperature, and take the reading, as appropriate. Conveniently, when the applications of the disposable device are carried out in an automatic instrument, the disposable device may comprise an additional trough for receiving priming fluid used to prime conduits in the instrument prior to running the actual analyte assay procedure. The additional priming trough will be located on the device at a region which is not in fluid communication with the assay path(s) present in the device. Finally, for purposes of device and sample identification, a bar code may be placed in one area of the top or bottom plate.

The device will now be further described in terms of the figures. In FIG. 1 is depicted an overhead view of an assay path 2 with a main channel 4 and two side reagent channels, 6 & 8. The main flow channel begins at the sample receiving region directly below the sample addition port 10. The sample addition port may be any convenient shape for receiving sample into the main channel, such as square, rectangular, oval or circular, usually circular. The dimensions of the sample addition port will be sufficiently large to receive a volume of sample, where the volume of sample will usually range from 20 to 2000 µl. The diameter of the sample addition port may range from 0.2 to 1.0 cm, but will typically range from about 0.475 to 0.5 cm. Typically, at least a portion of the main channel will be a capillary, wherein by capillary is meant that the dimensions of the main flow path provide for capillary flow of fluid through the flow path or channel. To provide for capillary flow, the height of the flow path will typically range from 0.02 to 2.5 mm, usually ranging from about 0.1 to 0.5 mm.

In fluid communication with sample receiving region 10 is main reagent area 12. The main reagent area may be any convenient shape, e.g. square, rectangular, oval or circular. Depending on the particular cartridge design, a particular shape of reagent chamber may be preferred. For example, where the reagent chamber comprises an impeller agitation means, a circular reagent chamber would be preferred. The volume of the reagent area will be sufficient to accept substantially all of the sample volume, in addition to any reagent which may be stored in the reagent area. The reagent area may comprise troughs for storing the reagent (not shown). Main reagent area 12 is separated from transport channel 14 by capillary valve 16. Fluid in the main transport channel 14 flows into incubation area 18. The distance between the top and bottom walls of the reagent area will be slightly greater than the distance between the top and bottom walls of the main transport channel and incubation area, ranging from 0.5 to 2.5 mm, usually 1.0 to 1.5 mm. The distance between the top and bottom walls of the main transport channel and incubation area will typically ranges from about 0.02 to 2.5 mm, more usually between about 0.1 and 0.5 mm. The incubation area may house an assay platform (not shown), where at least a portion of the steps of the signal producing system occur. Adjacent to the incubation area is a waste area 20. The dimensions of the waste area will not necessarily provide for capillary flow. The height of the waste area will range from 0.6 to 7.5 cm, the width of the waste area will range from 0.3 to 2.5 cm, and the depth of the waste area will range from 0.002 to 6.5 cm. The waste reservoir may conveniently have a vent which serves to release air and other gasses as fluid enters the waste area. Fluid from the waste area may be removed from the device periodically by external means. For example, the vent may also serve as an interface with an external suction means, e.g. a pump. The waste area may comprise various means for enhancing fluid flow through the flow paths of the device. Such means may include an absorptive membrane (not shown) which absorbs liquid from the incubation area. Alternatively, one may provide for a wicking means for removing liquid which has entered the waste area, thereby increasing the volume available for occupation by additional liquid from the device.

Side reagent channel 6 begins in liquid receiving region 22 which is directly below the liquid addition port (not shown). The dimensions of the liquid addition port will be sufficient to accommodate a drop of liquid having a volume ranging from 5.0 to 50 µl. The dimensions of the side reagent channel will provide for capillary flow through the channel, where the height will range from about 0.5 to 2.5 mm. In fluid communication with region 22 is side reagent area 24. The side reagent area is analogous to the main reagent area and may comprise agitation means as well as troughs (not shown) for storing reagent. The side reagent area will be large enough to accommodate the liquid introduced into the side reagent pathway, as well as any reagent stored in the area or agitation means present in the area, where the volume of the area will usually range from 50 to 150 µl, more usually from 65–70 µl. Separating side reagent reservoir 24 from side transport channel 26 is capillary valve 28. Side transport channel 26 opens into main transport channel 14 at entrance 30. Second side reagent channel 8 comprises, in the direction of fluid flow, second liquid receiving region 32 and second side reagent area 34.

The assay paths comprising the main and side reagent channels of the cartridge will be in a housing, where the housing will usually be made of two plates, which will be sealed together. Conveniently, one plate will serve primarily as a cover and provide the various ports and optical window (s), while the other plate will provide the various structures necessary for the reservoirs and channels associated with the device. Therefore, the plate into which the various reservoirs and channel are molded will usually be thicker than the cover plate, generally about 1.5–2-fold thicker than the cover plate.

The plates may be molded out of various plastics which allow for reasonably accurate tolerances, can withstand the various chemicals involved, and will allow for the presence of an optically-clear area. Materials of interest include glasses and plastics. Plastics which fulfill these requirements include acrylate, polystyrene, e.g. Dow 666 polystyrene, polycarbonate, SAN, ABS, etc. Materials can be treated to provide for better wetting characteristics, flow and biological receptor adherence. Methods of treating the plates may include protein binding, gamma irradiations, plasma etching, sugar coating, surface texture modification, e.g. roughening the surface, and the like.

Figure 2:
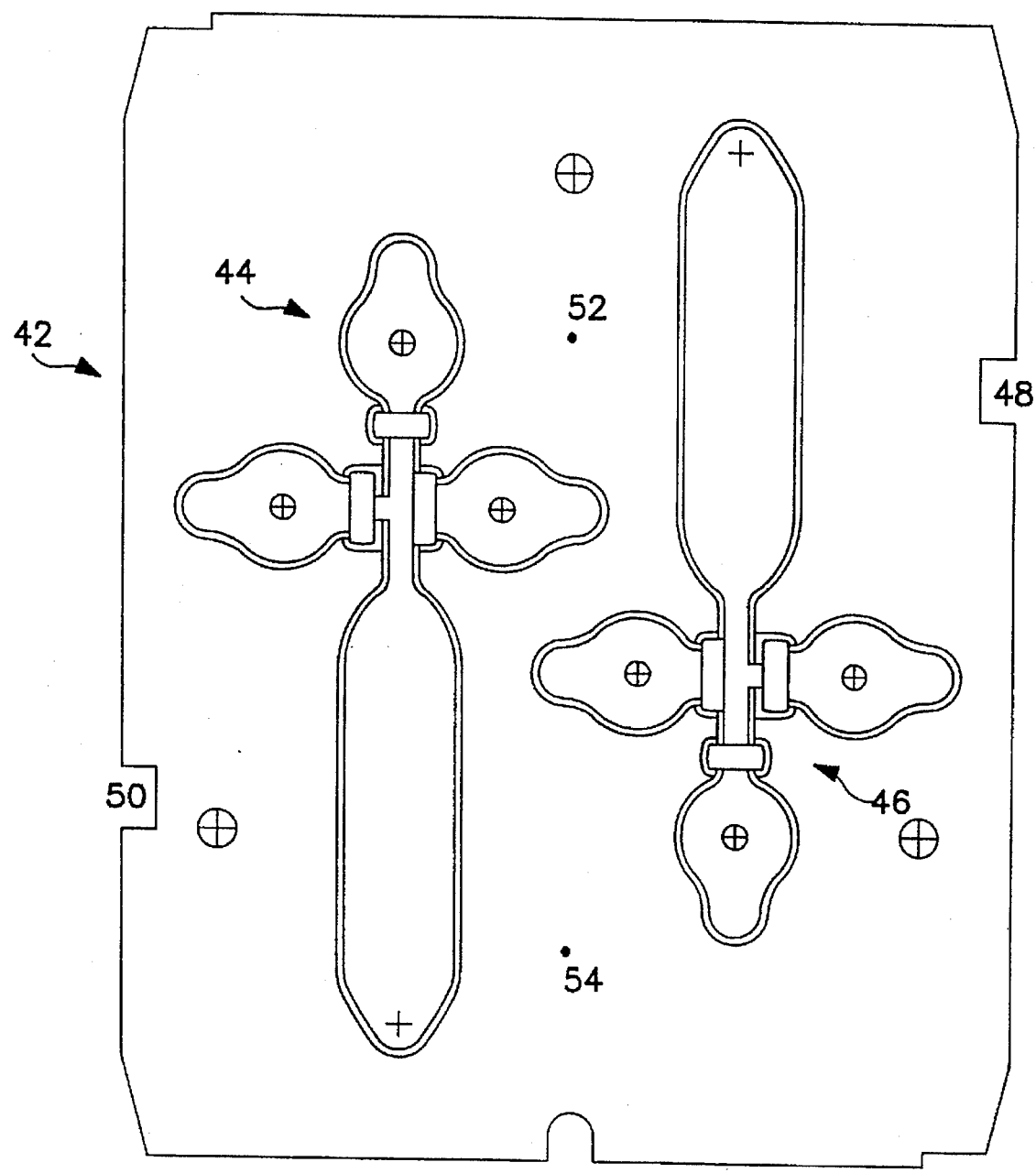
FIG. 2 is an overhead view of the bottom plate of a device in accordance with the subject invention.

In FIG. 2 is depicted a 2-dimensional, overhead view of a bottom plate 42. Bottom plate 42 shows one possible configuration comprising assay pathways 44 and 46 in opposing relationship. The sides of plate 42 comprise notches 48 & 50 for aligning and securing bottom plate 42 to the top plate. Also present are detents 52 & 54 for aligning and locking the bottom plate with the top plate.

Figure 3:
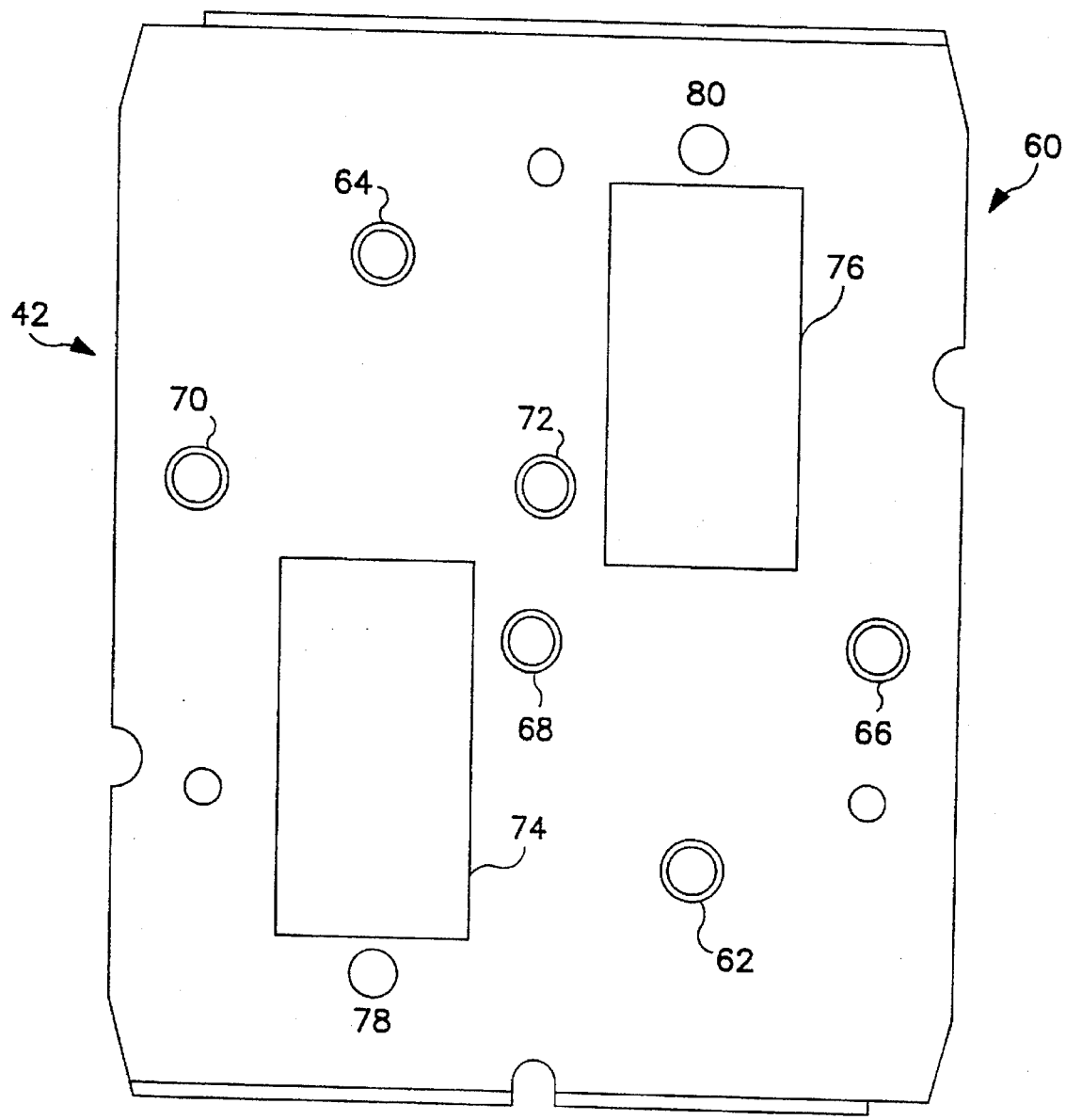
FIG. 3 is an overhead view of the top plate of the device in accordance with the subject invention.

In FIG. 3 is depicted top plate 60 which would correspond to bottom plate 42 of FIG. 2. Top plate 60 comprises sample addition ports 62 and 64 directly above the sample receiving regions of the two main channels beneath. Liquid addition ports, 66,68,70 and 72 provide means for introducing liquid into the side reagent pathways below. Optically clear windows 74 & 76 provide means for viewing the signal generated in the incubation area below. Present on the optically clear windows may be protrusions which safeguard the window from scratches during manufacture and handling. Air vents 78 and 80 provide outlet means for air and other gases from the waste reservoirs below. The air vents may also provide for connection with an external suction means for enhancing fluid flow through the device.

Figure 4:
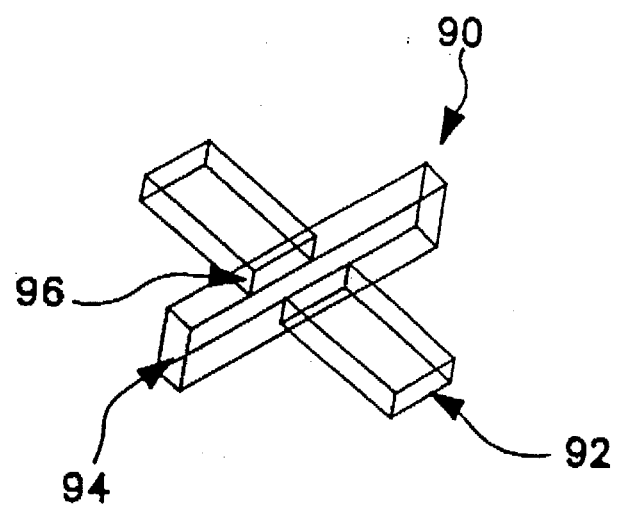
FIG. 4 is a three dimensional view of a capillary valve in accordance with the invention.

In FIG. 4 is depicted a three dimensional view of one embodiment of the capillary valve which may be employed in the subject device. Capillary valve 90 comprises flow path 92 (e.g. main or side reagent flow path) and control capillary 94 at right angles to each other, so that control capillary 94 intersects flow path 92 at intersection 96. As can be seen from the drawing, the control capillary disrupts the main flow path in a trough like area. The angle of descent from the floor of the flow path to the floor of the control capillary will be fairly steep, being at least 60°, preferably 90°. This intersection disrupts fluid flow in flow path 92 when control capillary 94 is empty, but does not impede fluid flow through flow path 92 when it is full. Thus, in using the capillary valve, one controls flow in the intersected flow path by emptying or filling the control capillary as appropriate. in another embodiment (not shown) the capillary valve is simply a depression in the flow path which is sufficiently deep to impede forward fluid flow across the depression. Typically, the angle of descent into the depression will be greater than about 60°, and will more usually be about 90°.

Figure 5:
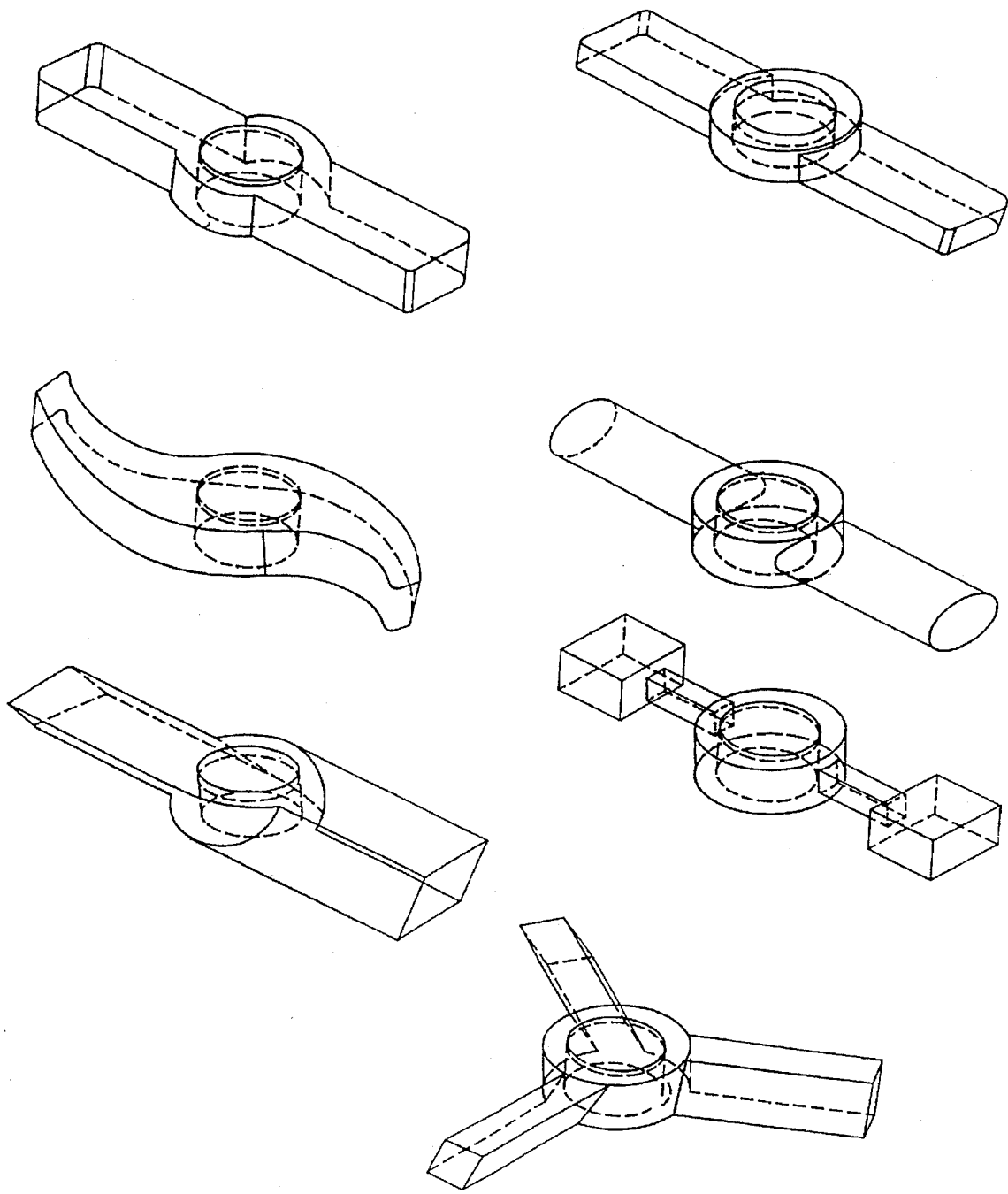
FIG. 5 provides three dimensional representations of various impeller structures in accordance with the subject invention.

In FIG. 5 are several three dimensional views of impeller configurations suitable for use as agitation means in the subject device. In the impeller, the various propeller arm configurations are positioned on a central axis which provides for clockwise and counterclockwise rotation. Thus, when the propeller arm is rotated on the axis, turbulence or agitation is created in its vicinity.

Figure 6:
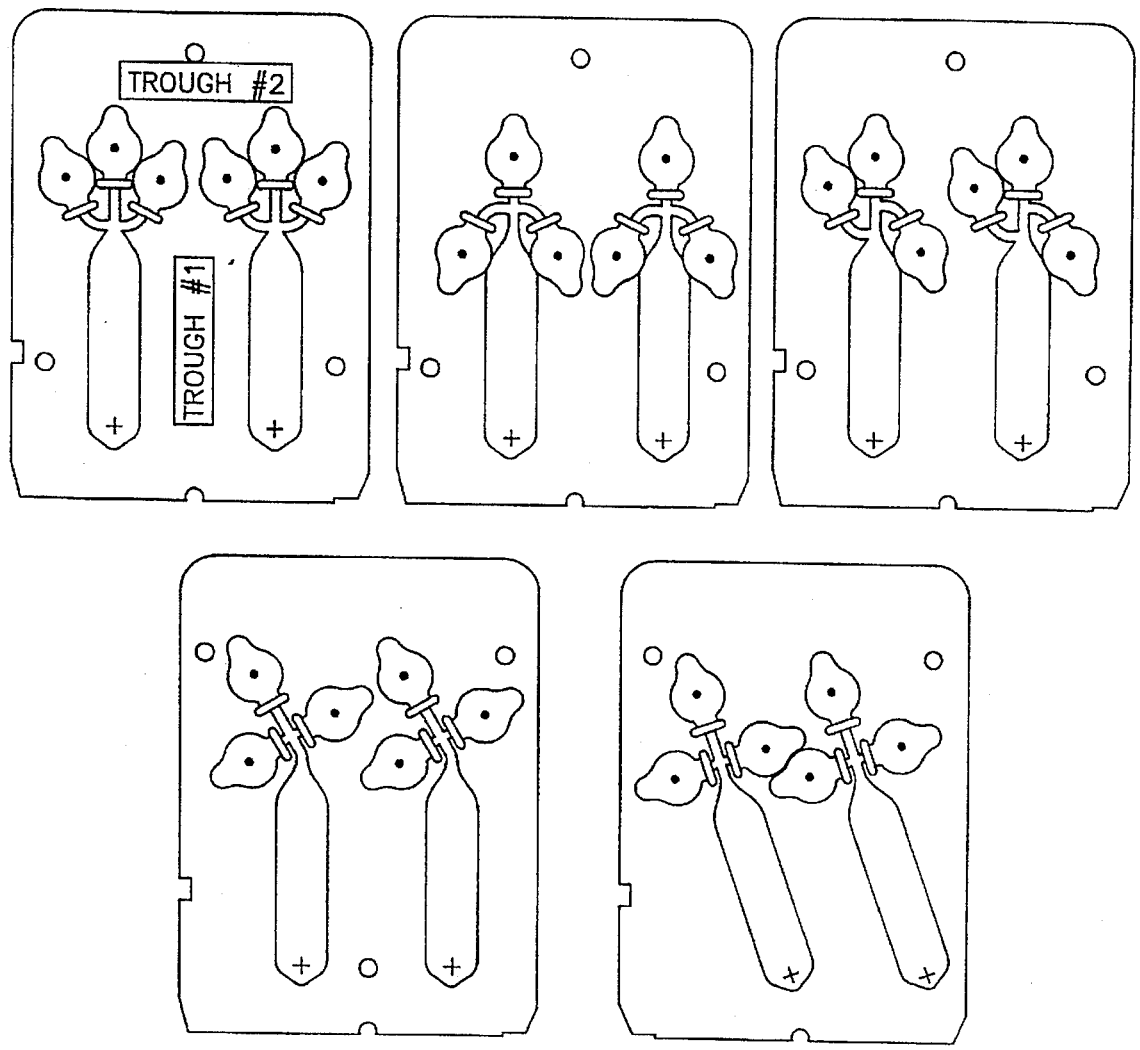
FIG. 6 depicts alternative bottom plate designs in accordance with the subject invention.

In FIG. 6 are several two dimensional views of various bottom plate configurations, where it is shown that the side reagent flow paths may be positioned in a variety of orientations in relation to the main flow path.

Figure 7:
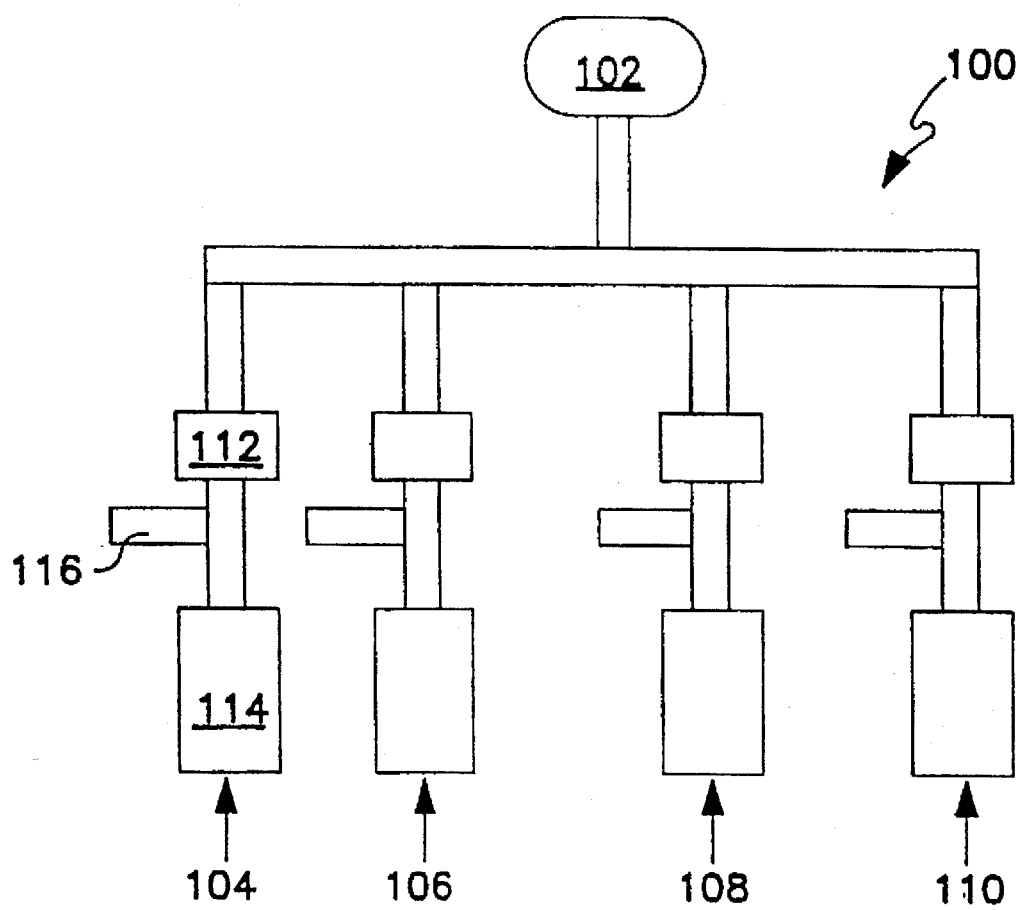
FIG. 7 is an overhead view of an alternative embodiment of an assay path of the subject invention.

FIG. 7 provides a two dimensional top view of the assay path of an alternative embodiment of the subject invention. Assay path 100 originates in sample addition port 102. The sample which enters the sample addition port diverges into a plurality of main channels, 104, 106, 108, 110. Main channel 104 will be described in greater detail, it being representative of the other main channels. Sample first enters main reagent area 112. From main reagent area 112, sample flows into incubation area 114. Side reagent channel 116 allows for introduction of wash fluid or additional reagent into main channel 104.

Figure 8:
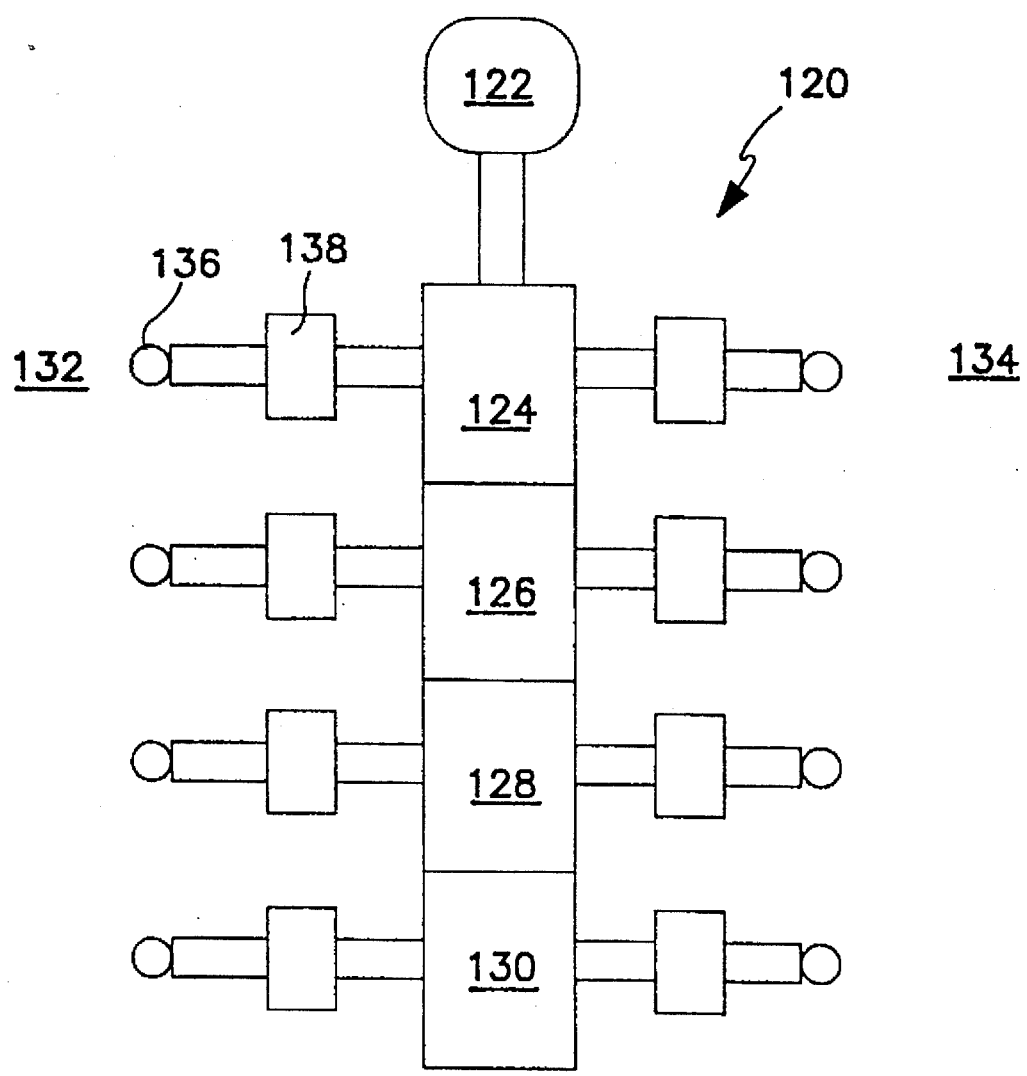
FIG. 8 is an overhead view of an alternative embodiment of an assay path of the subject invention.

FIG. 8 provides a two dimensional, top view of the assay path of another alternative embodiment of the subject invention. Assay path originates in sample addition port 122. Sample flows from sample addition port through a plurality of incubation areas 124, 126, 128 and 130 sequentially. Incubation area 124 will be further described, it being representative of each of the incubation areas. Side reagent channels 132 and 134 are in fluid communication with incubation area 124. Side reagent channel 132 comprises liquid addition port 136 and side reagent area 138.

To assemble the device, the appropriate reagents are placed at their proper sites, e.g. coating the surface of the troughs in the reagent areas. The necessary members of the signal producing system, e.g. binding pair members, lipid layers, fluorescence production layers and the like, are positioned on the assay platform using conventional means. After the reagents have been positioned, the top housing can be placed in registry over the bottom housing and the edges sealed by any appropriate means, such as ultrasonic welding, adhesives, gasket seals etc. The device is then ready to be stored for subsequent use. Where the device provides for two assays to be run, the two assay members can be used for a single assay and a control, for the same assay for two samples, or two different assays for the same or different samples. Thus, various configurations of protocols may be employed depending upon the nature of the desired assays. In addition, one may have a device with a single assay or a plurality of assays greater than two and one can vary the size appropriately, in accordance with the number of assays involved.

It is evident from the above that an improved disposable assay device for use in diagnostic assays is provided. The device provides for improved control over reagent mixing and fluid flow through the device. Further, the device requires minimal operator interaction and is simple to use. Despite the simplicity of use, the device provides for reliable and reproducible results. Finally, the configuration of the device is such that a wide variety of assays which employ diverse signal producing systems to obtain a detectable signal may be employed, providing for increased manufacturing scales and reduced unit cost.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A disposable assay device for use in analyte detection, said device comprising:
   a sample addition port in fluid communication with at least one main channel, wherein at least a portion of said main channel is a capillary and said main channel comprises:
   at least one reagent incubation area; and
   a waste area, wherein said waste area is downstream from said incubation area; and
   at least one side channel, said side channel comprising:
   a liquid addition port; and
   a side reagent area downstream from said liquid addition port;
   wherein said side reagent area of said side channel is in fluid communication with said main channel at a region of said main channel upstream from said waste area and wherein said device further comprises agitation means in at least one of said main channel or side reagent area.

2. The device according to claim 1, wherein said device further comprises at least one capillary valve positioned along said main channel or side reagent channel upstream from said incubation area.

3. The device according to claim 1, wherein said device comprises a plurality of main channels in fluid communication with said sample addition port.

4. The device according to claim 1, wherein said main channel comprises a plurality of incubation areas upstream from said waste area.

5. A disposable assay device for use in analyte detection in a fluid sample, said device comprising:
   a housing comprising top and bottom plates fastened together, wherein said fastened together top and bottom plates comprise:
   a sample addition port in fluid communication with a main channel comprising in a first direction of fluid flow from said sample addition port:
   a main reagent area comprising agitation means;
   a transport channel;
   an incubation area; and
   a waste area; wherein said main channel comprises at least one capillary valve upstream from said incubation area;
   a side reagent channel on either side of said main channel, wherein each of said side reagent channels comprised in a second direction of fluid flow:
   a liquid addition port;
   a side reagent area comprising agitation means; and
   a side reagent transport channel, wherein said side reagent transport channel is in fluid communication with said main channel at a region upstream from said waste area;
   an optically clear window above said incubation area; and
   members of a signal producing system in at least one of said main reagent channel and side reagent channels, wherein said signal producing system produces an optical signal which is related to the presence of analyte in said fluid sample.

6. The device according to claim 5, wherein at least a portion of said main channel is a capillary.

7. The device according to claim 5, wherein said agitation means is an impeller.

8. The device according to claim 5, wherein at least one of said side reagent channels comprises at least one capillary valve upstream from said main channel.

9. The device according to claim 5, wherein said main and side reagent areas comprise troughs comprising members of said signal producing system.

10. A disposable assay device for use in analyte detection in a fluid sample, said device comprising:
    a housing comprising a top and bottom plate fastened together, wherein said top and bottom fastened together plates comprise:
    at least one sample addition port, wherein said sample addition port is in fluid communication with an assay path, wherein said assay path comprises a main channel and one side channel on either side of said main channel, wherein at least a portion of said main channel is a capillary, said main channel comprising in a first direction of fluid flow from said sample addition port:
    a main reagent area comprising an impeller;
    a main transport channel;
    an incubation area;
    a waste area, wherein said waste area comprises a means for enhancing fluid flow through said device; and
    at least one capillary valve in said main channel at a region upstream from said incubation area; and
    said two side channels comprising in a second direction of fluid flow:
    a liquid addition port;
    a side reagent area comprising an impeller; and a side reagent transport channel, wherein said side reagent transport channel is in fluid communication with said main transport channel, wherein at least one of said side reagent channels further comprises at least one capillary valve upstream from said main channel;

an optically clear window above said incubation area, and members of a signal producing system in at least one of said main channel and side reagent channel, wherein said signal producing system produces an optical signal which is related to the presence of analyte in said fluid sample.

11. The device according to claim 10, further comprising a reference region which is not in fluid communication with said assay path.

12. The device according to claim 10, further comprising a priming trough which is not in fluid communication with said assay path.

* * * * *